United States Patent
Mallozzi et al.

(10) Patent No.: US 7,573,267 B1
(45) Date of Patent: Aug. 11, 2009

(54) SYSTEM AND METHOD FOR ACTIVE MR TRACKING

(75) Inventors: Richard Philip Mallozzi, Ballston Lake, NY (US); Charles Lucian Dumoulin, Ballston Lake, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 12/017,006

(22) Filed: Jan. 19, 2008

(51) Int. Cl.
*G01V 3/00* (2006.01)
(52) U.S. Cl. .................................... 324/307; 324/318
(58) Field of Classification Search ................. 324/307, 324/318, 301; 600/410
See application file for complete search history.

(56) References Cited

U.S. PATENT DOCUMENTS

| | | | | |
|---|---|---|---|---|
| 5,271,400 A | | 12/1993 | Dumoulin et al. | |
| 6,002,256 A | * | 12/1999 | Slade | 324/322 |
| 6,166,540 A | * | 12/2000 | Wollin | 324/300 |
| 2003/0146750 A1 | * | 8/2003 | Vaughan, Jr. | 324/318 |
| 2005/0195084 A1 | * | 9/2005 | Dimmer et al. | 340/572.7 |

\* cited by examiner

*Primary Examiner*—Brij B. Shrivastav
*Assistant Examiner*—Megann E Vaughn
(74) *Attorney, Agent, or Firm*—Joseph J. Christian

(57) ABSTRACT

A system and method for active MR tracking includes a magnetic resonance imaging (MRI) system having a plurality of gradient coils positioned about a bore of a magnet, an RF coil assembly positioned in the bore, and a pulse module. The MRI system also includes a polarization reversal switch controlled by the pulse module to transmit RF signals to the RF coil assembly coupled to the polarization reversal switch and an RF switch controlled by the pulse module to transmit the RF signals to the polarization reversal switch.

18 Claims, 4 Drawing Sheets

SYSTEM AND METHOD FOR ACTIVE MR TRACKING

BACKGROUND OF THE INVENTION

The present invention relates generally to medical procedures in which a device is inserted into a body, and more particularly to tracking of such device with the use of magnetic resonance signals.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a rotating magnetic field (excitation field $B_1$) which is in the x-y plane and which is rotating near the Larmor frequency, the net aligned moment, or "longitudinal magnetization", $M_z$, may be rotated, or "tipped", into the x-y plane to produce a net transverse magnetic moment $M_t$. When such a rotating magnetic field is applied for a finite duration, the resulting pulse is termed an "excitation rf pulse". The net transverse magnetic moment created by the excitation RF pulse also rotates at the Larmor frequency and continues after the excitation RF pulse is terminated. This transverse magnetic moment creates a detectable MR signal that may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Using an alternate sequence of measurement cycles it is possible to determine the location of a device placed within a body. In one such sequence one or more small MR receive coils acquire MR signals in the presence of a magnetic field gradient ($G_x$, $G_y$ or $G_z$). Fourier analysis is applied to the detected MR signal to determine the frequency of the signal. Since the signal is acquired in the presence of a selected magnetic field gradient and since the signal is detected with a small receive coil having limited spatial sensitivity, the frequency of the signal provides a measure of the coil's (and subsequently the device's) location. Using this or one of many other well-known active MR tracking techniques it is possible to rapidly determine the three-dimensional coordinates of one or more coils.

While tracking an active device in a fluid having a long longitudinal relaxation time, T1, such as blood, the signal is decreased because of the reduction of longitudinal polarization associated with the long T1 and the rapid application of RF excitation pulses. Under some conditions, such as in an environment of high flow rate, this leads to compromised tracking capability. For example, in the atrial chambers of the heart, which are of large interest for electrophysiology procedures, tracking capability can be less than ideal.

Also, spins that are not near the active device can generate MR signals that couple to volume RF coils in the scanner, such as the radio-frequency body coil. These signals can then couple back to the tracking coils. The result is that spins that are not near the device are detected. Under conditions of low signal-to-noise, this confounding signal interferes with the localized signal desired from the device and tends to compromise the device tracking.

It would therefore be desirable to have a system and method capable of reducing interference to tracking signals when tracking an active device in an MR scan. It would also be desirable to have a system and method capable of robust tracking in the presence of moving blood having a long longitudinal relaxation time, T1.

BRIEF DESCRIPTION OF THE INVENTION

The present invention provides a system and method of tracking an active device that overcome the aforementioned drawbacks. A polarization reversal switch reverses the sense of rotation of the rotating magnetic field created by an RF coil assembly to generate a counter-rotating magnetic field for use during active tracking.

According to an aspect of the present invention, an MRI apparatus includes a magnetic resonance imaging (MRI) system having a plurality of gradient coils positioned about a bore of a magnet, an RF coil assembly positioned in the bore, and a pulse module. The MRI system also includes a polarization reversal switch controlled by the pulse module to transmit RF signals to the RF coil assembly coupled to the polarization reversal switch and an RF switch controlled by the pulse module to transmit the RF signals to the polarization reversal switch.

According to another aspect of the present invention, a method of active MR tracking includes inserting an MR tracking coil into a region of interest and generating an RF signal capable of causing an RF coil assembly to generate a B1 excitation magnetic field. A polarization of the RF signal is reversed, and the reverse polarized RF signal is transmitted to the RF coil assembly to generate a counter-rotating B1 excitation magnetic field within the region of interest. The method further includes inducing current in the MR tracking coil with the counter-rotating B1 excitation magnetic field to create a linearly polarized magnetic field near the MR tracking coil and acquiring MR signals excited by the linearly polarized magnetic field near the MR tracking coil.

According to yet another aspect of the present invention, a computer readable storage medium having stored thereon a computer program comprising instructions which when executed by a computer cause the computer to generate an RF excitation signal and reverse a polarization of the RF excitation signal. The instructions further cause the computer to transmit the reverse polarized RF signal to an RF coil assembly for generation of a counter-rotating magnetic field within a region of interest such that spins localized to a tracking coil are excited and acquire MR signals from the excited localized spins.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
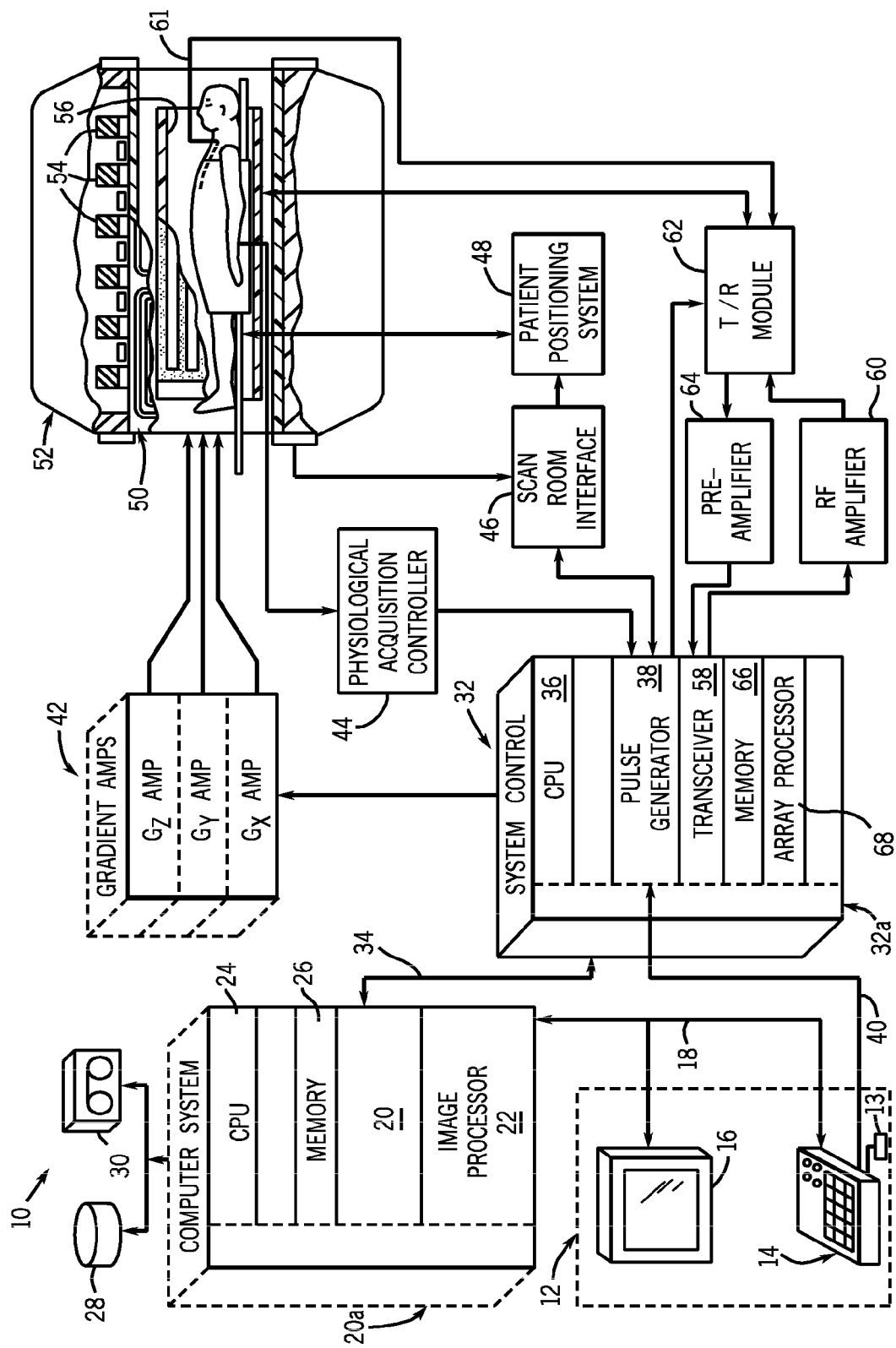
FIG. 1 is a schematic block diagram of an MR imaging system incorporating the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to either the RF coil 56 or a tracking coil 61 by a transmit/receive (T/R) module 62. The resulting signals emitted by the excited nuclei in the patient may be sensed by either RF coil 56 or tracking coil 61 and coupled through the T/R module 62 to a preamplifier 64. The amplified MR signals are demodulated, filtered, and digitized in the receiver section of the transceiver 58. The T/R module 62 is controlled by a signal from the pulse generator module 38 to electrically connect the RF amplifier 60 to either the coil 56 or the tracking coil 61 during the transmit mode and connects the preamplifier 64 to either the RF coil 56 or the tracking coil 61 during the receive mode. In this manner, RF coil 56 or tracking coil 61 may be controlled to both transmit and receive signals, or either RF coil 56 or tracking coil 61 may be controlled to transmit while the other is controlled to receive.

The MR signals picked up by either the RF coil 56 or the tracking coil 61 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands from him received from the operator console 12, this image data may be archived in long term storage, such as on the tape drive 30, or it may be further processed by the image processor 22 and conveyed to the operator console 12 and presented on the display 16.

Figure 2:
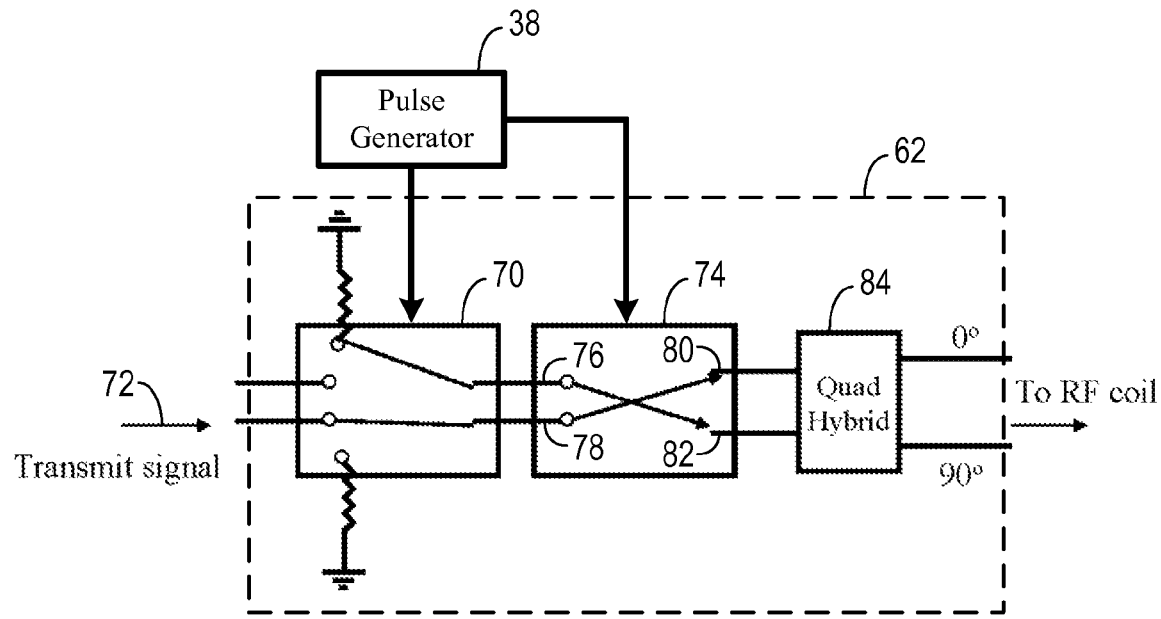
FIGS. 2-3 are schematic block diagrams of a transmit/receive module according to an embodiment of the present invention.
Figure 3:
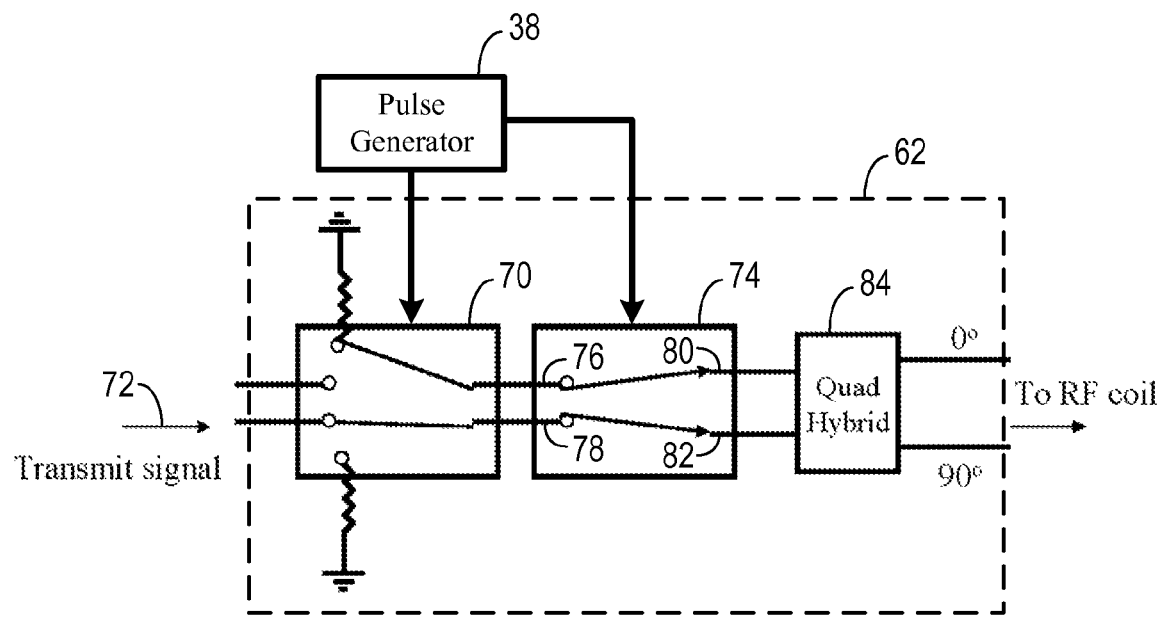

FIGS. 2 and 3 shows a schematic block diagram of a portion of T/R module 62 (shown in FIG. 1) configured to control RF coil 56 according to an embodiment of the present invention. T/R module 62 includes a T/R switch 70 configured to receive a transmit signal 72 from RF amplifier 60 (shown in FIG. 1). T/R switch 70 is coupled to and controlled by pulse generator 38 to transmit or receive RF signals. Coupled to T/R switch 70 is a polarization reversal switch 74 having a pair of inputs 76, 78 and a pair of outputs 80, 82. Polarization reversal switch 74 is also controlled by pulse generator 38, which configures the switch 74 to operate in either a normal polarization transmit mode or a reverse polarization transmit mode. Accordingly, polarization reversal switch 74 is capable of causing the RF coil 56 to generate either a clockwise or counter-clockwise rotating B1 excitation field. As shown in FIG. 2, polarization reversal switch 74 is operated in the reverse polarization transmit mode such that input 76 is coupled to output 82 and input 78 is coupled to output 80. As shown in FIG. 3, polarization reversal switch 74 is operated in the normal polarization transmit mode such that input 76 is coupled to output 80 and input 78 is coupled to output 82.

A quadrature hybrid module 84 is coupled to polarization reversal switch 74 and is coupled to RF coil 56. As shown in FIGS. 2 and 3, quadrature hybrid module 84 receives transmit signal 72 from polarization reversal switch 74 for splitting transmit signal 72 into two components, a 0 degrees component signal and a 90 degrees component signal. When operating in the reverse polarization transmit mode as shown in FIG. 2, polarization reversal switch 74 reverses a polarization of transmit signal 72 and delivers the reverse polarized signal to the quadrature hybrid module 84 for signal splitting. Once split, the reverse polarized signal is transmitted to RF coil 56 for generation of a magnetic field inside a bore of magnet assembly 52.

The reverse polarized signal causes RF coil 56 to generate a magnetic field having a reverse polarization according to a counter-rotating RF mode. Spins inside a region of interest (ROI) affected by RF coil 56 remain largely unaffected by the reverse polarization magnetic field. However, spins local to a tracking coil, such as tracking coil 61 of FIG. 1, are excited due to coupling between RF coil 56 and the tracking coil, which causes such localized spin excitation. MR data from such excited spins it may then be acquired either in RF coil 56 or the tracking coil for further processing and, preferably, for use in active tracking.

When operating in the normal polarization transmit mode as shown in FIG. 3, polarization reversal switch 74 maintains the polarization of transmit signal 72 and delivers the normal polarized signal to the quadrature hybrid module 84 for signal splitting. Once split, the normal polarized signal is transmitted to RF coil 56 for generation of a magnetic field inside a bore of magnet assembly 52.

The normal polarized signal causes RF coil 56 to generate a magnetic field having a normal polarization such that spins inside a region of interest (ROI) are globally affected by RF coil 56. MR data from a majority of the ROI may then be acquired via RF coil 56 or some other coil for further processing.

Figure 4:
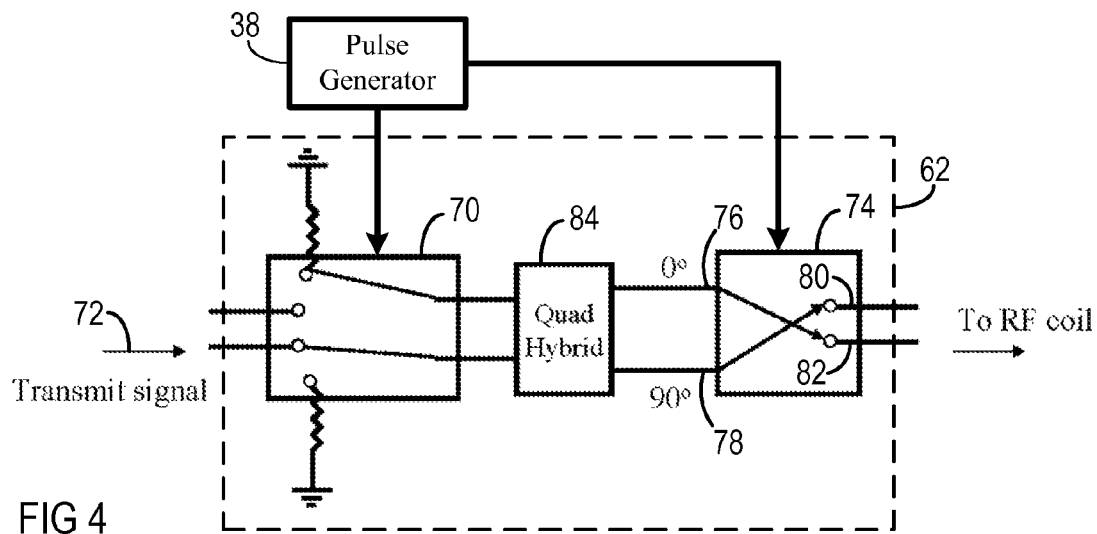
FIGS. 4-5 are schematic block diagrams of a transmit/receive module according to another embodiment of the present invention.
Figure 5:
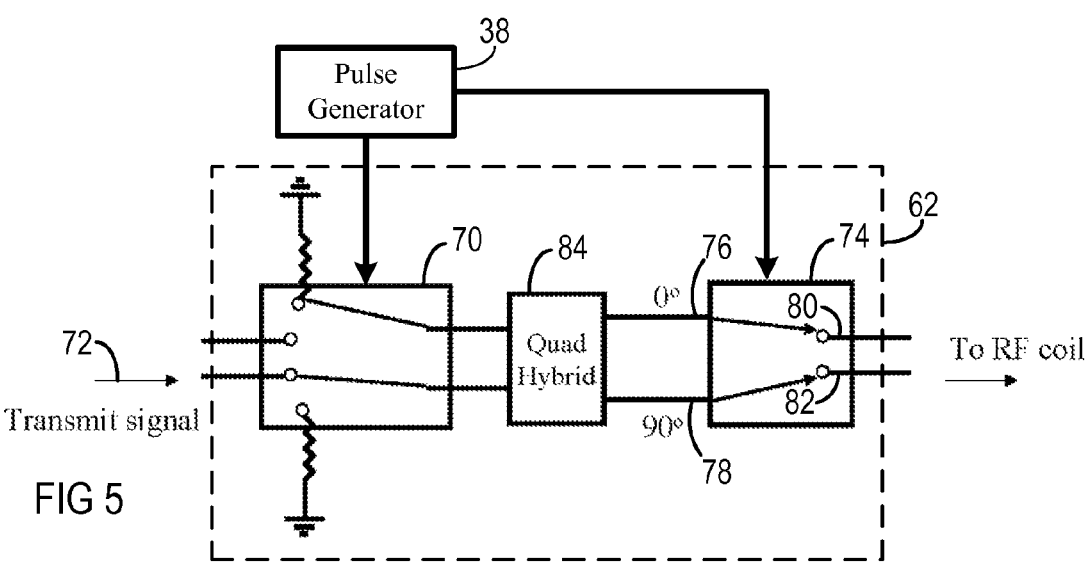

FIGS. 4 and 5 shows a schematic block diagram of a portion of T/R module 62 (shown in FIG. 1) configured to control RF coil 56 according to another embodiment of the present invention. Similar to the embodiment shown in FIGS. 2 and 3, the embodiment shown in FIGS. 4 and 5 include a T/R switch 70, a polarization reversal switch 74, and a quadrature hybrid module 84. However, instead of having the polarization reversal switch 74 coupled between the T/R switch 70 and the quadrature hybrid module 84, the embodiment shown in FIGS. 4 and 5 positions the quadrature hybrid module 84 to be coupled between the T/R switch 70 and the polarization reversal switch 74. Accordingly, the signal output from the quadrature hybrid module 84 has its polarization reversed (FIG. 4) or maintained (FIG. 5) for delivery to RF coil 56. Operation of the T/R module 62 shown in FIGS. 4 and 5 is as described above in FIGS. 2 and 3.

Figure 6:
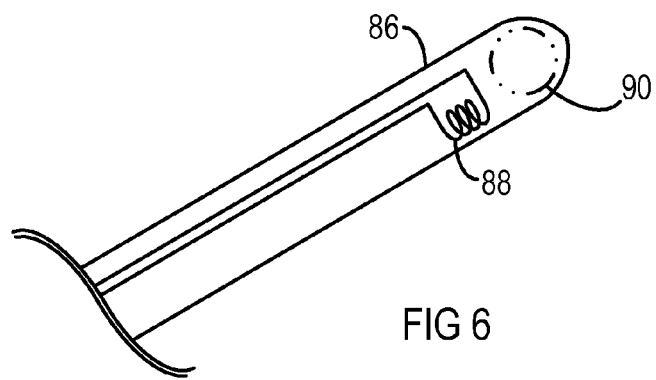
FIG. 6 is a schematic illustration of an MR tracking coil assembly according to an embodiment of the present invention.

FIG. 6 shows a tracking coil assembly 86 of a portion of tracking coil 61 (shown in FIG. 1) according to an embodiment of the present invention. Tracking coil assembly 86 includes a small RF coil 88 electrically coupled to T/R module 62. In one embodiment, when active and positioned in a counter-rotating magnetic field, RF coil 88 causes excitation of localized spins in tissue or other matter adjacent thereto. The counter-rotating magnetic field induces currents in RF coil 88, which in turn create an oscillation magnetic field having a dipole distribution. Since this field is created by a single coil, it is not circularly polarized. This linearly polarized magnetic field can be decomposed into two components: a rotating and a counter-rotating field. According to an embodiment of the present invention, the rotating component of the field creates transverse spin magnetization in the spin population near the MR tracking coil while the counter-rotating component of the field has no effect. In another embodiment, tracking coil assembly 86 includes an MR active sample 90, and RF coil 88 causes excitation of localized spins in the MR active sample 90 as well as the tissue or other matter adjacent thereto when active and positioned in a counter-rotating magnetic field.

Figure 7:
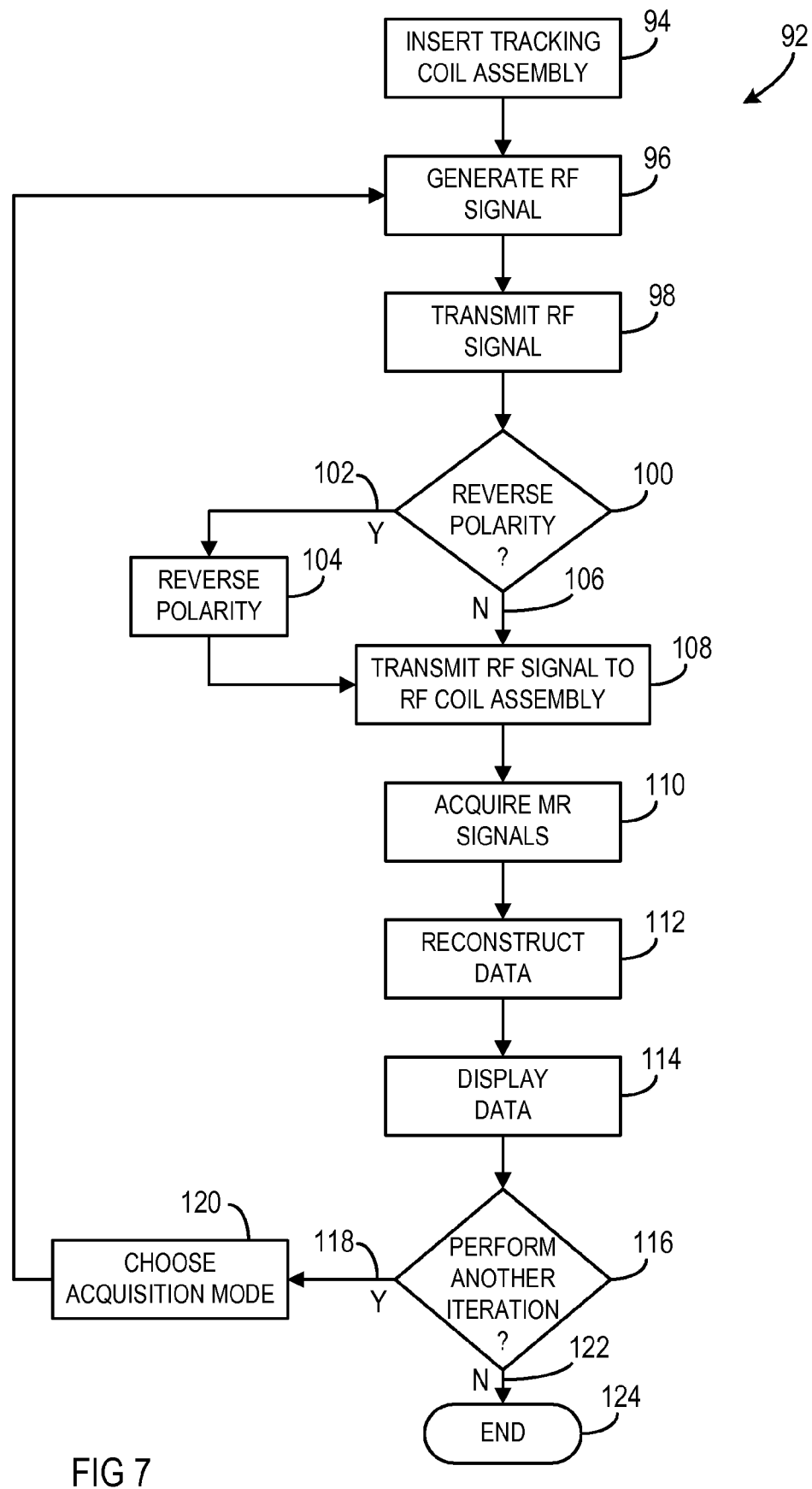
FIG. 7 is a flowchart illustrating a technique for active tracking according to an embodiment of the present invention.

FIG. 7 shows a technique 92 for active MR tracking according to embodiment of the present convention. Technique 92 begins with inserting or positioning a tracking coil assembly, such as the tracking coil assembly 86 shown in FIG. 6, into a region of interest (ROI) such as a cardiac or other region of a patient at STEP 94.

At STEP 96, an RF signal is generated that is capable of causing an RF coil assembly to generate a rotating magnetic field. The RF signal is transmitted at STEP 98 to a polarization reversal switch that is controlled to maintain or reverse a polarity of the RF signal. At STEP 100, technique 92 determines whether a polarity of the RF signal should be maintained or reversed. If technique 92 is in a tracking mode 102, then a pulse module operates the polarization reversal switch to reverse the polarity of the RF signal at STEP 104. If technique 92 is in an imaging mode 106, then the pulse module operates the polarization reversal switch to maintain a polarity of the original RF signal, and process control continues to STEP 108.

At STEP 108, the RF signal, whether having a normal polarization or a reversed polarization, is transmitted to an RF coil assembly for generation of a rotating magnetic field. In one embodiment of the present invention, the RF coil assembly is an RF body coil assembly. In another embodiment, the RF coil assembly is the tracking coil assembly 86. The RF coil assembly is configured to generate either a rotating or a counter-rotating magnetic field based on the polarity of the RF signal transmitted thereto. For example, if at STEP 104, the RF signal had its polarity reversed, then the RF coil assembly will generate a counter-rotating magnetic field. However, if the polarity of the RF signal was not reversed, then the RF coil assembly will generate a normal or rotating magnetic field that rotates in a direction opposite to the counter-rotating magnetic field. According to an embodiment of the present invention, the rotating magnetic field excites a global spin population within the ROI while the counter-rotating magnetic field couples the tracking coil assembly with the RF coil assembly for exciting spins local to the tracking coil assembly. In this manner, the reverse polarization or counter-rotating magnetic field suppresses spin information outside an area local to the tracking coil assembly. It is contemplated that the spins local to the tracking coil assembly may occur in tissue surrounding the tracking coil assembly or may occur in an active sample position adjacent to an MR tracking coil within the tracking coil assembly.

At STEP 110, MR data are acquired from the ROI. If technique 92 is in a tracking mode, then MR data are acquired from excited spins local to the tracking coil assembly 86. If technique 92 is in an imaging mode, then MR data are acquired from the global population of excited spins within the ROI. In one embodiment of the present invention, the RF body coil assembly acquires the MR data at STEP 110. In another embodiment, the tracking coil assembly 86 acquires the MR data at STEP 110. Following acquisition of the MR data at STEP 110, data is reconstructed from the acquired MR data at STEP 112. If technique 92 is in an imaging mode, then the reconstructed data forms an image. If technique 92 is in a tracking mode, then the reconstructed data forms a tracking point. The reconstructed data is displayed to a user at STEP 114. If technique 92 is in an imaging mode, then the reconstructed data is displayed as an image. If technique 92 is in a tracking mode, then the reconstructed data is displayed as an icon at the tracked location within an image and/or the numerical values of the location of the MR tracking coil are displayed or sent for further processing. According to an embodiment of the present invention the reconstructed data is displayed together with data reconstructed during a previous mode. That is, if technique 92 acquired MR data during an imaging mode, the reconstructed image of the acquired imaging mode MR data is preferably displayed together with acquired tracking mode MR data acquired in a previous iteration as a combined or overlaid image. Likewise, if technique 92 acquired MR data during a tracking mode, the reconstructed image of the acquired imaging mode MR data is preferably displayed together with acquired imaging mode MR data acquired in a previous iteration as a combined or overlaid image.

Following display of the combined image at STEP 114, technique 92 determines whether to perform another acquisition iteration at STEP 116. If another acquisition iteration is to be performed 118, technique 92 chooses an acquisition mode for the subsequent iteration at STEP 120. In one embodiment of the present invention, the imaging and tracking acquisition modes are interleaved such that the tracking modes are alternated between iterations. However, it is contemplated that multiple imaging acquisition modes or multiple tracking acquisition modes may be performed before performing the other acquisition mode. Process control and then proceeds to STEP 96 for performing another iteration of STEPS 96-114 as described above. If another acquisition iteration is not to be performed 122, then process control ends 124.

A technical contribution for the disclosed method and apparatus is that it provides for a computer implemented system and method for tracking an active device having spins outside a region local to the active device not contribute to MR data acquired during a tracking mode.

An advantage of embodiments of the present invention includes the reverse polarization mode not exciting the global spin population, which suppresses background interference from global spins that may confound MR tracking. A counter-rotating magnetic field induces an oscillation current in an MR tracking coil that in turn creates a linearly polarized magnetic field in the MR tracking coil's immediate surroundings. This linearly polarized magnetic field can be decomposed into two components, a rotating and a counter-rotating field. The rotating component of the field creates transverse spin magnetization in the spin population near the MR tracking coil while the counter-rotating component of the field has minimal effect in the spin population far from the MR tracking coil.

Additionally, for tracking in long T1 fluids such as blood, the larger, global spin population maintains a large longitudinal polarization while enabling a larger tracking signal local to the tracking coil such that saturation effects may be minimized. That is, a population of fresh spins that have a large longitudinal magnetization is constantly entering the excitation volume of the tracking coils, leading to an increase in the MR signal.

It is contemplated that one skilled in the art would recognize that reversal of the sense of circular polarization can also be achieved without a quadrature hybrid and polarization reversal switch by using two transmitting chains operating 90 degrees out of phase with respect to each other. In such a configuration, the selection of rotating or counter-rotating fields can be accomplished by exchanging the relative phases of the two transmitting chains.

Therefore, according to an embodiment of the present invention, an MRI apparatus includes a magnetic resonance imaging (MRI) system having a plurality of gradient coils positioned about a bore of a magnet, an RF coil assembly positioned in the bore, and a pulse module. The MRI system also includes a polarization reversal switch controlled by the pulse module to transmit RF signals to the RF coil assembly coupled to the polarization reversal switch and an RF switch controlled by the pulse module to transmit the RF signals to the polarization reversal switch.

According to another embodiment of the present invention, a method of active MR tracking includes inserting an MR tracking coil into a region of interest and generating an RF signal capable of causing an RF coil assembly to generate a B1 excitation magnetic field. A polarization of the RF signal is reversed, and the reverse polarized RF signal is transmitted to the RF coil assembly to generate a counter-rotating B1 excitation magnetic field within the region of interest. The method further includes inducing current in the MR tracking coil with the counter-rotating B1 excitation magnetic field to create a linearly polarized magnetic field near the MR tracking coil and acquiring MR signals excited by the linearly polarized magnetic field near the MR tracking coil.

According to yet another embodiment of the present invention, a computer readable storage medium having stored thereon a computer program comprising instructions which when executed by a computer cause the computer to generate an RF excitation signal and reverse a polarization of the RF excitation signal. The instructions further cause the computer to transmit the reverse polarized RF signal to an RF coil assembly for generation of a counter-rotating magnetic field within a region of interest such that spins localized to a tracking coil are excited and acquire MR signals from the excited localized spins.

The present invention has been described in terms of the preferred embodiment, and it is recognized that equivalents, alternatives, and modifications, aside from those expressly stated, are possible and within the scope of the appending claims.

What is claimed is:

1. An MRI apparatus comprising:
a magnetic resonance imaging (MRI) system having a plurality of gradient coils positioned about a bore of a magnet;
an RF coil assembly positioned in the bore;
a pulse module;
a polarization reversal switch controlled by the pulse module to transmit RF signals to the RF coil assembly coupled to the polarization reversal switch, wherein the polarization reversal switch is configured to operate in either a normal polarization transmit mode or a reverse polarization transmit mode, thereby causing the RF coil assembly to generate either a clockwise or counter-clockwise rotating B1 excitation field;
an RF switch controlled by the pulse module to transmit the RF signals to the polarization reversal switch.

2. The MRI apparatus of claim 1 further comprising a quadrature hybrid module coupled to the polarization reversal switch.

3. The MRI apparatus of claim 2 wherein the quadrature hybrid module is configured to transmit the RF signals from the RF switch to the polarization reversal switch.

4. The MRI apparatus of claim 2 further comprising a tracking assembly positioned in the bore and having an MR tracking coil.

5. The MRI apparatus of claim 4 wherein the RF coil assembly is a body coil assembly.

6. The MRI apparatus of claim 4 further comprising a computer readable storage medium having stored thereon a computer program comprising instructions which when executed by a computer cause the computer to cause the pulse module to operate the polarization reversal switch in a reverse polarization transmit mode such that the body coil assembly generates a reverse polarization magnetic field from the RF signals.

7. The MRI apparatus of claim 6 wherein the instructions further cause the computer to acquire MR signals received in the MR tracking coil after the reverse polarization magnetic field has been generated.

8. The MRI apparatus of claim 7 wherein the instructions further cause the computer to acquire MR signals received in the body coil assembly after the reverse polarization magnetic field has been generated.

9. The MRI apparatus of claim 6 wherein the instructions further cause the computer to cause the pulse module to operate the polarization reversal switch in a normal polarization transmit mode such that the body coil assembly generates a normal polarization magnetic field from the RF signals.

10. The MRI apparatus of claim 9 wherein the instructions further cause the computer to acquire MR signals received in the body coil assembly after the normal polarization magnetic field has been generated.

11. The MRI apparatus of claim 4 wherein the tracking assembly further comprises an active sample positioned adjacent to the MR tracking coil.

12. A method of active MR tracking comprising:
(A) inserting an MR tracking coil into a region of interest;
(B) generating an RF signal capable of causing an RF coil assembly to generate a B1 excitation magnetic field;
(C) reversing a polarization of the RF signal;
(D) transmitting the reverse polarized RF signal to the RF coil assembly to generate a counter-rotating B1 excitation magnetic field within the region of interest;
(E) inducing current in the MR tracking coil with the counter-rotating B1 excitation magnetic field to create a linearly polarized magnetic field near the MR tracking coil;
(F) acquiring MR signals excited by the linearly polarized magnetic field near the MR tracking coil;
(G) generating a second RF signal capable of causing an RF coil assembly to generate a rotating B1 excitation magnetic field;
(H) maintaining a polarization of the RF signal;
(I) transmitting the RF signal having its polarization maintained to the RF coil assembly to generate a non-counter-rotating B1 excitation magnetic field; and
(J) acquiring MR signals excited via the non-counter-rotating B1 excitation magnetic field.

13. The method of claim 12 wherein the step of acquiring comprises acquiring the MR signals via the MR tracking coil.

14. The method of claim 12 wherein the step of acquiring comprises acquiring the MR signals via the RF coil assembly.

15. The method of claim 12 further comprising interleaving a first execution of steps (B)-(F) and a second execution of steps (G)-(J) during an MR scan.

16. The method of claim 12 wherein the step of inserting comprises inserting the MR tracking coil into a cardiac region of a patient.

17. A method of active MR tracking comprising:
(A) inserting an MR tracking coil into a region of interest;
(B) generating an RF signal capable of causing an RF coil assembly to generate a B1 excitation magnetic field;
(C) reversing a polarization of the RF signal;
(D) transmitting the reverse polarized RF signal to the RF coil assembly to generate a counter-rotating B1 excitation magnetic field within the region of interest;
(E) inducing current in the MR tracking coil with the counter-rotating B1 excitation magnetic field to create a linearly polarized magnetic field near the MR tracking coil;
(F) acquiring MR signals excited by the linearly polarized magnetic field near the MR tracking coil,
wherein the step of reversing comprises controlling a polarization reversal switch to reverse a polarity of the RF signal, further comprising splitting the RF signal into separate phase components prior to reversing the polarization of the RF signal.

18. A computer readable storage medium having stored thereon a computer program comprising instructions which when executed by a computer cause the computer to:
generate an RF excitation signal;
split the RF excitation signal into separate phase components;
reverse a polarization of the RF excitation signal;
operate a polarization reversal switch in a reverse polarization transmit mode;
transmit the reverse polarized RF excitation signal to an RF coil assembly for generation of a counter-rotating magnetic field within a region of interest such that spins localized to a tracking coil are excited;
acquire MR signals from the excited localized spins.

* * * * *